United States Patent
Ashburn

[19]

[11] Patent Number: 6,055,450
[45] Date of Patent: Apr. 25, 2000

[54] BIFURCATED GAMMA CAMERA SYSTEM

[75] Inventor: William L. Ashburn, La Jolla, Calif.

[73] Assignee: Digirad Corporation, San Diego, Calif.

[21] Appl. No.: 09/028,962

[22] Filed: Feb. 23, 1998

Related U.S. Application Data

[63] Continuation-in-part of application No. 08/694,819, Aug. 9, 1996, Pat. No. 5,742,060, which is a continuation-in-part of application No. 08/372,807, Dec. 23, 1994, abandoned.

[51] Int. Cl.[7] ........................................... A61B 6/00
[52] U.S. Cl. ................ 600/431; 250/363.05; 250/363.04
[58] Field of Search ..................... 600/436, 431; 378/62, 68; 250/370.08, 370.09, 363.01, 363.02, 363.03, 363.04, 363.05

[56] References Cited

U.S. PATENT DOCUMENTS

| | | |
|---|---|---|
| 2,980,500 | 4/1961 | Miller et al. . |
| 3,188,594 | 6/1965 | Koller et al. . |
| 3,372,997 | 3/1968 | Bither et al. ................................ 23/315 |
| 3,390,090 | 6/1968 | Taylor et al. ........................... 252/62.3 |
| 3,418,471 | 12/1968 | Gydesen et al. . |
| 3,540,859 | 11/1970 | Taylor et al. ............................... 23/315 |
| 3,666,952 | 5/1972 | McCready et al. ................. 250/363.03 |
| 3,717,762 | 2/1973 | Grenier et al. ........................... 250/366 |
| 3,721,938 | 3/1973 | Entine et al. ............................... 338/15 |
| 3,999,071 | 12/1976 | Siffert et al. ............................. 250/370 |
| 4,047,037 | 9/1977 | Schlosser et al. ........................ 250/370 |
| 4,055,765 | 10/1977 | Gerber et al. ............................ 250/370 |
| 4,055,766 | 10/1977 | Miller et al. ............................. 250/370 |
| 4,243,885 | 1/1981 | Agouridis et al. ....................... 250/370 |
| 4,245,158 | 1/1981 | Burstein et al. ......................... 250/370 |
| 4,255,659 | 3/1981 | Kaufman et al. ........................ 250/370 |
| 4,292,645 | 9/1981 | Schlosser et al. ......................... 357/29 |
| 4,571,494 | 2/1986 | Nishiki et al. ........................... 250/370 |
| 4,633,881 | 1/1987 | Moore et al. ............................ 128/659 |
| 4,651,005 | 3/1987 | Baba et al. ............................. 250/360.1 |
| 4,672,207 | 6/1987 | Derenzo ................................ 250/363 S |
| 4,682,604 | 7/1987 | Fymat et al. ............................. 128/659 |
| 4,755,679 | 7/1988 | Wong .................................... 250/363 S |
| 4,794,257 | 12/1988 | Baba et al. ......................... 250/370.01 |
| 4,846,187 | 7/1989 | Siegel ...................................... 128/659 |
| 4,911,905 | 3/1990 | Weirauch ................................. 423/509 |
| 4,920,969 | 5/1990 | Suzuki et al. ............................ 128/659 |
| 4,950,897 | 8/1990 | Mandelis et al. ........................ 250/334 |
| 4,980,553 | 12/1990 | Henry ...................................... 250/369 |
| 5,005,195 | 4/1991 | Lanza et al. ............................... 378/62 |
| 5,007,427 | 4/1991 | Suzuki et al. ............................ 128/659 |
| 5,027,817 | 7/1991 | John ................................... 128/653 R |
| 5,036,201 | 7/1991 | Carroll et al. ......................... 250/363.1 |
| 5,057,690 | 10/1991 | Morgan et al. ....................... 250/336.1 |
| 5,072,458 | 12/1991 | Suzuki ....................................... 2/102 |

(List continued on next page.)

OTHER PUBLICATIONS

Butler, et al., Progress in cd1–xZnxTe (CZT) Radiation Detectors, MRS–93 Conference, Apr. 12, San Fransisco, CA, 1993.

Butler, et al., Recent developments in CdZnTe gamma ray detector technology, SPIE International Symposium, Jul. 19, San Diego, CA, 1992.

(List continued on next page.)

*Primary Examiner*—Brian L. Casler
*Attorney, Agent, or Firm*—Fish & Richardson P.C.

[57] ABSTRACT

The medical imaging system has first and second gamma camera heads. Each head has a front facing an examination field. The heads are articulatable between a first plurality of relevant orientations in which a first edge of the first head is aligned with the first edge of the second head in a parallel spaced-apart relation. A gap is defined between the first edges of sufficient dimension to accommodate a biomedical instrument.

28 Claims, 7 Drawing Sheets

U.S. PATENT DOCUMENTS

| | | | |
|---|---|---|---|
| 5,085,325 | 2/1992 | Jones et al. | 209/580 |
| 5,105,087 | 4/1992 | Jagielinski | 250/370.09 |
| 5,111,818 | 5/1992 | Suzuki et al. | 128/644 |
| 5,119,818 | 6/1992 | Carroll et al. | 128/659 |
| 5,132,542 | 7/1992 | Bassalleck et al. | 250/370.09 |
| 5,138,167 | 8/1992 | Barnes | 250/370.01 |
| 5,349,190 | 9/1994 | Hines et al. | 250/363.05 |
| 5,365,069 | 11/1994 | Eisen et al. | 250/370.09 |
| 5,367,169 | 11/1994 | Pierfitte | 250/363.05 |
| 5,376,795 | 12/1994 | Hasegawa et al. | 250/363.04 |
| 5,451,789 | 9/1995 | Wong et al. | 250/363.03 |
| 5,519,221 | 5/1996 | Weinberg | 250/363.02 |
| 5,523,571 | 6/1996 | Velazquez et al. | 250/363.05 |
| 5,591,977 | 1/1997 | Green et al. | 250/363.03 |
| 5,594,251 | 1/1997 | Fleury et al. | 250/363.05 |
| 5,595,177 | 1/1997 | Mena et al. | 128/653.1 |
| 5,663,566 | 9/1997 | Maniawski et al. | 250/363.04 |
| 5,742,060 | 4/1998 | Ashburn | 250/370.09 |
| 5,760,401 | 6/1998 | Nelleman et al. | 250/363.03 |
| 5,811,813 | 9/1998 | Maor | 250/363.05 |
| 5,844,241 | 12/1998 | Liu et al. | 250/363.04 |
| 5,961,457 | 10/1999 | Raylman et al. | 600/436 |
| 5,965,891 | 10/1999 | Weinberg | 250/363.02 |

OTHER PUBLICATIONS

Butler, et al., Cadmium Zinc Telluride Detectors for Industrial Radiation Measurement, and Topical Meeting on Industrial Radiation and Radioisotope Measurement Applications, Raleigh, Sep. 8, 1992.

Butler, et al., CdZnTe Detector Arrays for Nuclear Medicine Imaging, IEEE Nuclear Science, Nov. 2, San Fransisco, CA, 1993.

Butler, et al., Cd1–xZnxTe Detector Imaging Array, SPIE Medical Imaging, Feb. 14, New Port, CA 1993.

Entine, G., et al., Cadmium Telluride Gamma Camera, IEEE Transactions on Nuclear Sci., NS–26(1), Feb., 1979.

Entine, G., et al., Review of CdTe Medical Applications, Ue De Physique, pp. 354.

Goldstein, R., Clinical Experience With Rubidium–82 Pet Imaging, Cardio, pp. 74–87, Mar. 1990.

Kaufman, et al., Semiconductor Gamma–Cameras in Nuclear Medicine, IEEE Transactions on Nuclear Science, Ns–27(3):1073, Jun. 1980.

McCready, et al., Clinical tests on a prototype semiconductor gamma–camera, British Journal of Radiology, 44(517):58, Jan. 1971.

Narra, et al., A Neutral Technetium–99m Complex for Myocardial Imaging, The Journal of Nuclear Science, 30: 1830, 1989.

Profio, et al., Semiconductor Camera for Detection of Small Tumors, 16(1):53, 1975.

Seldin, et al., Myocardial Perfusion Imaging with Technetium–99m SQ30217: Comparison with Thallium–201 and Coronary Anatomy, The Journal of Nuclear Medicine, 30:312, 1989.

Shapiro, et al., Detailed Concept Review of the Data Push Architecture Test Chip Analog Design, SLAC TN–93–4, pp. 2–15, Mar. 1993.

Positron Emission Tomography, Cardiology, Jun. 1990.

Stewart, et al., Myocardial Clearance Kinetics of Technetium–99m–SQ30217: A Marker of Regional Myocardial Blood Flow, The Journal of Nuclear Medicine, 31(7):1183, Jul. 1980.

Yarema, et al., A High Performance Multi–Channel Preamplifier Asic*, IEEE Transactions On Nuclear Science, 39(4):1992.

BIFURCATED GAMMA CAMERA SYSTEM

CROSS-REFERENCE TO RELATED APPLICATIONS

This application is a continuation-in-part of U.S. patent application Ser. No. 08/694,819, filed Aug. 9, 1996 U.S. Pat. No. 5,742,060 entitled "Medical System for Obtaining Multiple Images of a Body from Different Perspectives", which is a continuation-in-part of U.S. patent application Ser. No. 08/372,807, filed Dec. 23, 1994 entitled "Semiconductor Gamma-Ray Camera and Medical Imaging System", the disclosures of which are incorporated herein by reference.

BACKGROUND

1. Technical Field

The present invention relates generally to medical imaging and, more particularly, to imagers which detect gamma ray emissions from radionuclides administered to a patient.

2. Background Information

The field of medical imaging includes use of photon detectors commonly known as "gamma cameras" to detect, record, and display the uptake and distribution of radioactive drugs administered orally or intravenously to a patient. Signals generated by the gamma cameras are processed to provide a display of the internal distribution of the drugs in the patient or a particular target area or organ of the patent. The images are then interpreted by a specialist in radiology, cardiology or other relevant fields, in diagnosing any of a variety of medical conditions.

SUMMARY

A medical imaging system according to one aspect of the invention includes first and second gamma camera heads, each having a front facing an examination field. The heads are articulatable between a first plurality of relative orientations in which an inboard edge of the first head is aligned with an inboard edge of the second head in a parallel spaced-apart relation defining a gap therebetween. The gap is of sufficient dimension to permit a biomedical instrument to pass through the gap. The system may include a biomedical instrument, such as a biopsy needle, bearing a radionuclide tag for emitting radiation of a type detectable by the heads. The instrument may be passable through the gap between the heads and into the examination field. A protective sleeve may be provided passing through the gap and having a first end facing the examination field and a second end facing away from the examination field. The sleeve may have a presterilized internal surface, so that when the instrument passes through the sleeve the operative end of the instrument does not come in contact with the heads and thus cannot directly acquire a contaminant from the heads. Alternatively the instrument may enter the field without passing between the heads.

The heads may be hinged to each other for relative movement about an axis fixed relative to the heads such as by a first hinge located at one end of the inboard edges of the heads and a second hinge located at a second end of the inboard edges of the heads. The second head may be readily removable from the first head. The first head may be directly supported by a gantry and the second head may be indirectly supported by the gantry via the first head.

One or more monitors may be provided for displaying images representative of emissions received by the heads. A display may be provided for generating a stereoscopic image of emissions received by the heads. The display may comprise a pair of goggles having left and right display sections. The display may simultaneously display a pair of images on a single screen which are separated by eyewear worn by a user.

According to another aspect of the invention, a method for guiding a biomedical instrument to a target in a body includes: providing a radionuclide source at the target; providing a radionuclide tag on the instrument; providing a gamma camera detector system for receiving and detecting emissions from the source and the tag; viewing at least one image generated from the emissions; and moving the instrument so that a perceived target location and a perceived tag location converge in the image.

The detector may comprise two detector arrays having convergent fields of view. The arrays may respectively be formed on two detector heads. The heads may be articulatable between a plurality of relative orientations. The heads may be provided with removable collimators which determine the fields of view of the respective heads. The positioning and orienting of the heads and the selection of collimator angles may be made so as to substantially fill the fields of view with a selected region. This allows relatively small movements of the instrument to yield relatively large perceived movements across the fields of view of the heads and across the images displayed on monitors. The selected region may extend at least from the target to a point of entry of the instrument into the body or to a region of approach of the instrument to the body. The positioning and orienting of the heads may serve to maximize image quality within the region. The instrument may be moved so that the perceived tag location and target location converge in images from both heads.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

Figure 1:
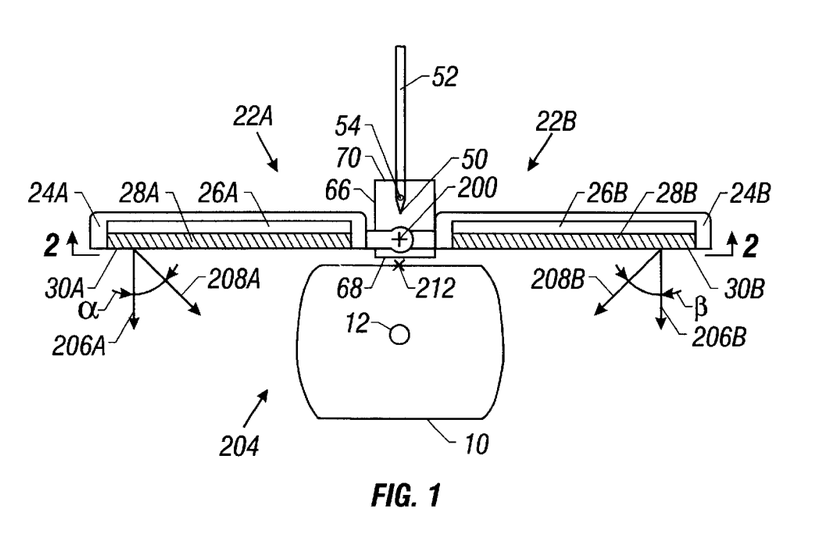
FIG. 1 is a partial, semi-schematic, top cross-sectional view of a gamma camera system.

FIG. 1 shows one embodiment of a bifurcated gamma camera system having a pair of detector heads 22A and 22B. Each detector head includes a housing 24A, 24B which holds a planar detector array 26A, 26B. Immediately in front of the detector array is a collimator 28A, 28B. A front face 30A, 30B of the collimator substantially forms the front face of the detector head.

Figure 2:
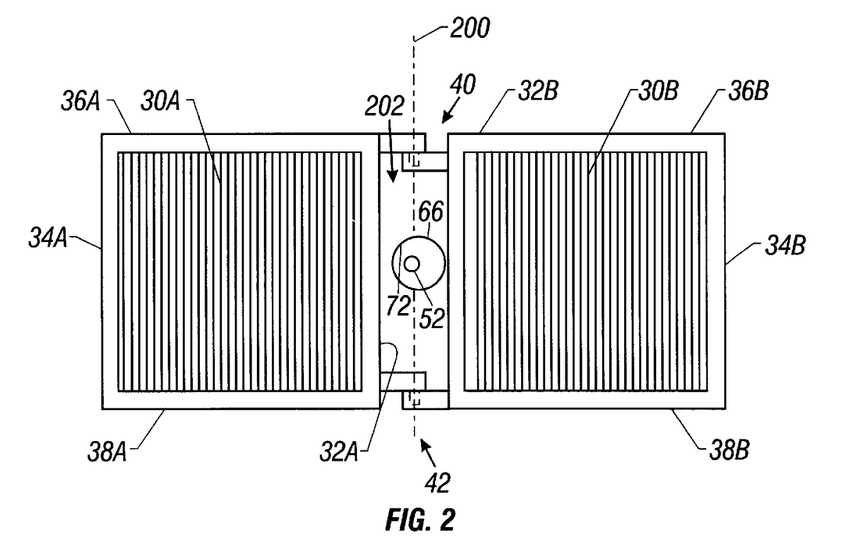
FIG. 2 is a partial, semi-schematic, front view of the gamma camera system of FIG. 1, taken along line 2—2.

As shown in FIG. 2, each detector head has an inboard edge 32A, 32B, an outboard edge 34A, 34B, a top edge 36A, 36B and a bottom edge 38A, 38B. In the illustrated embodiment, the inboard and outboard edges are parallel to each other and perpendicular to the top and bottom edges, with the overall plan of the detector heads being substantially square.

As shown in FIG. 2, the detector heads are hinged to each other by a pair of upper and lower hinges 40 and 42 located at upper and lower ends of the inboard edges 32A, 32B of the heads. In the illustrated embodiment, the hinges have a single hinge axis 200 which is fixed relative to the heads. The hinges 40 and 42 hold the inboard edges 32A, 32B of the heads aligned with each other in a parallel spaced-apart relation so as to create a gap 202 between and bounded by the edges 32A, 32B and the hinges 40 and 42. The heads face an examination field 204 which contains the body 10 of a patient or study subject.

The collimators 28A and 28B have respective collimator angles α and β, defined as the angle between a surface normal direction 206A, 206B and the collimation or view direction 208A, 208B, with a positive angle being measured inward from the surface normal. The collimators admit only incident radiation approaching the detector at a specific range or ranges of angles of incidence with the detector. As shown in the figures, the collimators admit incident radiation which is substantially parallel to the collimation directions 208A and 208B, respectively, of the detector heads 22A and 22B.

Figure 3:
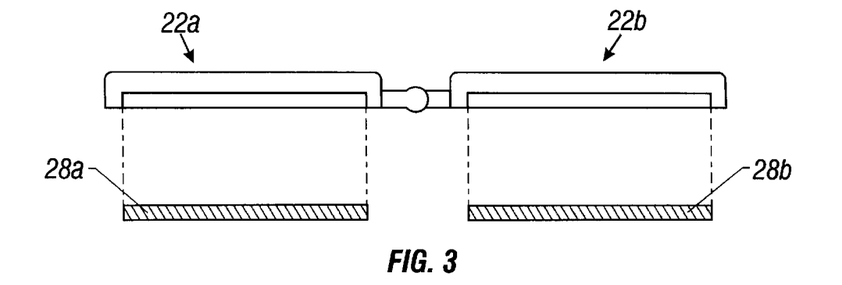
FIG. 3 is a partial, semi-schematic, top view of the gamma camera system of FIG. 1, shown with collimators removed.

As shown in FIG. 3, the collimators 28A, 28B may be removable from the associated head 22A, 22B so as to allow the replacement by a collimator of a desired collimation angle.

Figure 4:
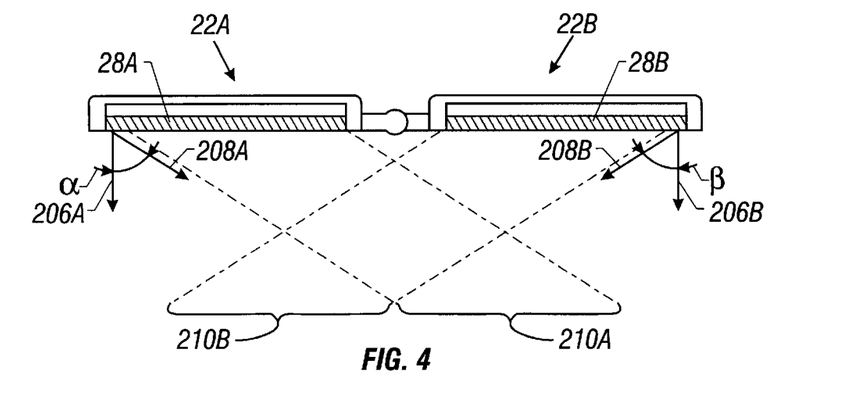
FIG. 4 is a partial, semi-schematic, top view of the gamma camera system of FIG. 1 showing fields of view of the detector heads.

As further shown in FIG. 4, the collimation angle α, β determines the field of view 210A, 210B of the detector head.

Figure 5:
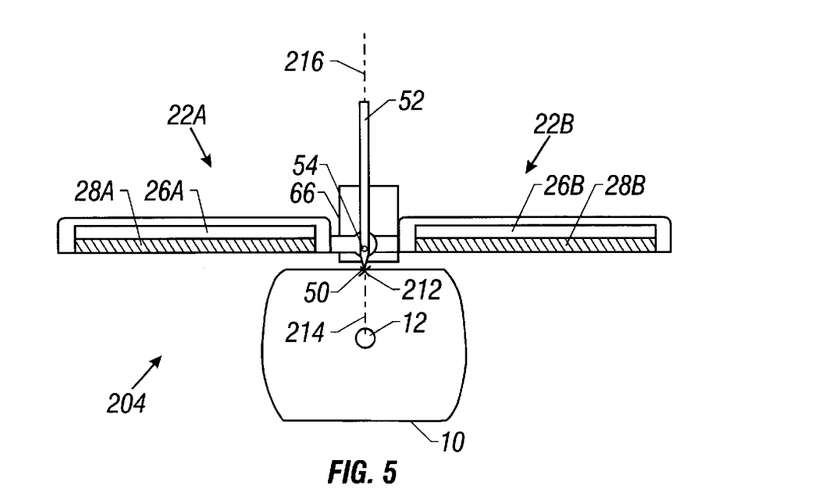
FIG. 5 is a partial, semi-schematic, top cross-sectional view of the gamma camera system of FIG. 1.

In an exemplary process for using the gamma camera system, as shown in FIG. 5, the tip 50 of a biopsy needle 52 or other instrument is guided to a target such as a tumor 12 within the body 10 of a patient for removing at least a piece of the tumor. It is assumed that the location of the tumor is already known and that the tumor has been tagged with a radionuclide drug. The needle tip has its own radionuclide tag 54, which like the radionuclide drug used to tag the tumor emits radiation of a type detectable by the detector arrays 26A and 26B.

A first set up portion of the process involves the positioning of the gamma camera heads 22A and 22B relative to each other and relative to the patient and the selection of collimator angles α and β, for each head. With the tumor or target location known, the point of entry 212 of the needle 52 to the body 10 and the path 214 from the point of entry 212 to the target 12 are often dictated or substantially influenced by anatomical factors. In a typical case, the path will be a straight line between the point of entry and the target. In order to achieve that path, typically the approach path 216 of the needle to the point of entry will be a continuation of that straight line path 214. For image clarity it is desirable to bring the modules as close to the target as possible, which means as close to the body perimeter as possible. Especially when the target is not centrally located within the body this will result in locating the line of approach asymmetrically relative to the modules. The choice of collimator angles and positions of the heads 22A and 22B may then be made so as to maximize the size of a desired viewing domain within the field of view of the respective camera heads. This allows that small movements of the needle 52 may result in relatively large movements across the field of view when an image is displayed.

Figure 6:
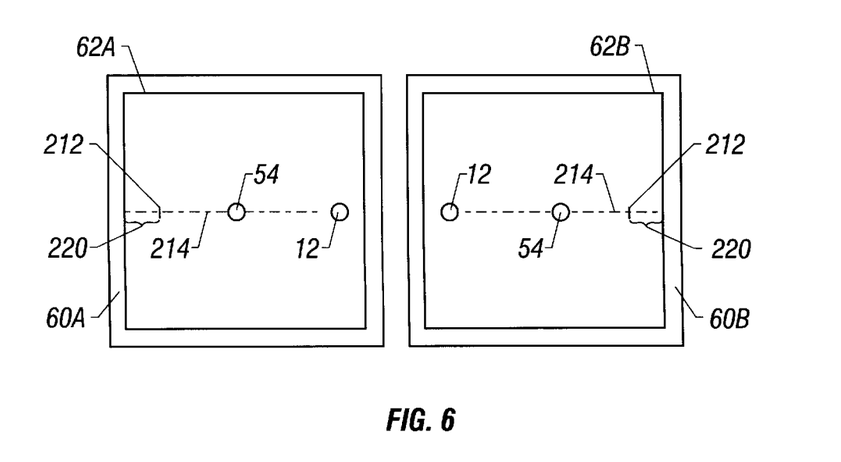
FIG. 6 is a partial, semi-schematic front view of a pair of monitors displaying images representative of emissions received by the detector heads of a gamma camera system.
Figure 7:
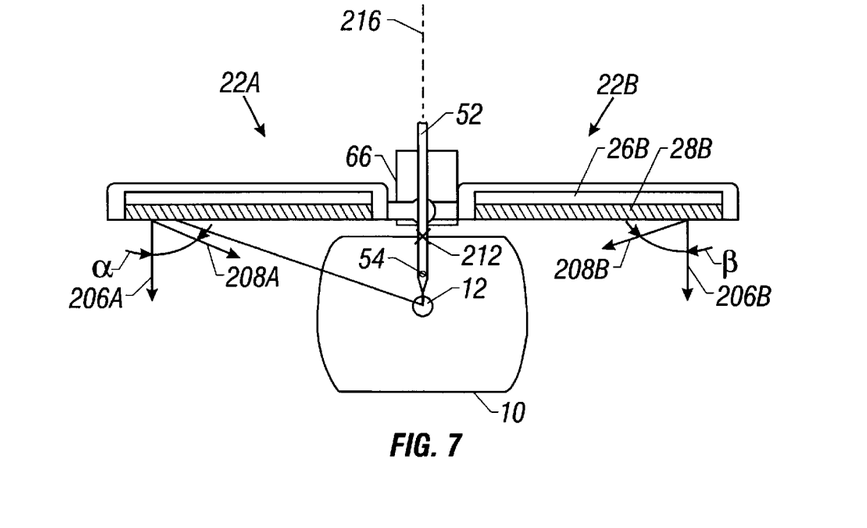
FIG. 7 is a partial, semi-schematic, top cross-sectional view of a gamma camera system.

By way of example, as shown in FIG. 6, first and second monitors 60A and 60B may be provided for displaying images which represent the emissions received by the respective first and second detector arrays 26A and 26B. The image 62A, 62B on each monitor 60A, 60B may correspond to the field of view of the associated detector array 26A, 26B, although a magnified view of only a portion of the field of view may be provided. For example, with the detector halves in the parallel orientation of FIGS. 4, 5 and 7, the collimator angles α and β, may be chosen so that, as shown in FIG. 6, the fields of view of the first and second detectors are substantially filled by a region extending from the target 12 to the point of entry 212 and to a region of approach 220 of the needle to the body.

Returning to FIGS. 1, 2 and 5, to perform the exemplary biopsy, the biopsy needle 52 may be introduced from without the examination field 204 such as from behind the detector heads 22A and 22B. The needle 52 may be inserted through a protective sleeve 66 which passes through the gap 202. The sleeve has a first open end 68 facing the examination field 204 and a second open end 70 facing away from the examination field. The sleeve has at least a presterilized internal surface 72. Thus the needle may pass through the second end 70 of the sleeve, through the sleeve, and out through the first end 68 of the sleeve to a location within the examination field. In this way, the tip 50 of the needle 52 can come into contact only with the presterilized internal surface 72. The tip 50 does not come into contact with the gamma camera heads and thus cannot directly acquire a contaminant from the heads. The sleeve may be fixed to one or both of the heads and may be formed of a flexible material. The user may then bring the tip 50 substantially to the point of entry 212. At this point the user should be able to see the tag 54 and the target 12 on both monitors 60A and 60B. The user then moves the needle so that the perceived locations of the tag 54 and target 12 converge in both images 62A and 62B. This results in the needle tip moving from the point of entry 212 along the path 214 to the target 12. When the tag 54 and target 12 are coincident in both images, the needle tip is within the target and the biopsy sample may be taken. The needle 52 may then be withdrawn along the path 214 and removed from the patient.

Figure 8:
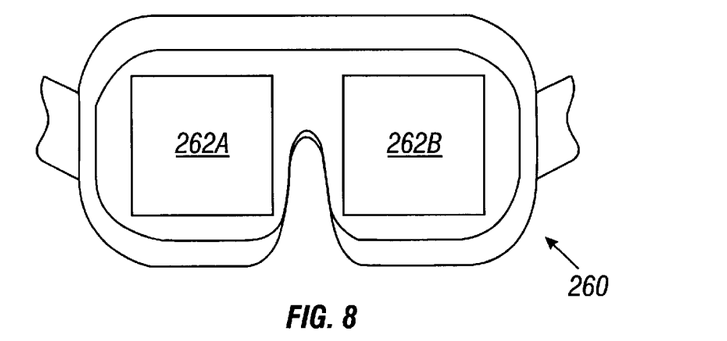
FIG. 8 is a partial, semi-schematic, inside view of display goggles for displaying images representative of emissions received by the detector heads of a gamma camera system.
Figure 9:
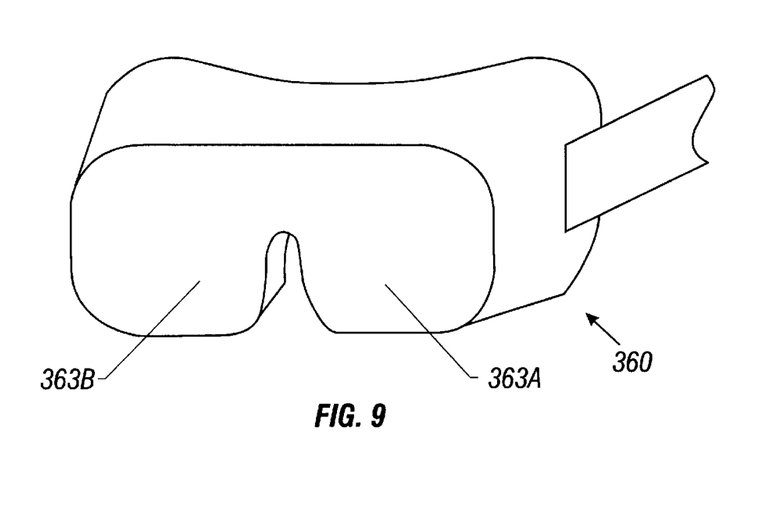
FIG. 9 is a partial, semi-schematic, front view of eyewear for stereoscopically viewing a displayed image representative of emissions received by the detector heads of a gamma camera system.

Optionally, the system may be configured to provide the user with a 3-dimensional or stereoscopic view. For example, images from the detector heads 26A and 26B may be provided to left and right eye pieces 262A and 262B of a pair of goggles 260 or other eyewear (FIG. 8). In such a case, the positioning of the camera modules and selection of the collimator angles as well as any processing of the signals from the camera modules may be specifically configured so as to provide as close as possible to a true 3-dimensional view. Another stereoscopic option involves the simultaneous display of two images on a single screen. As shown in FIG. 9, images may be separated by use of eyewear 360 with different color filters 363A, 363B in front of each of the user's eyes.

Figure 10:
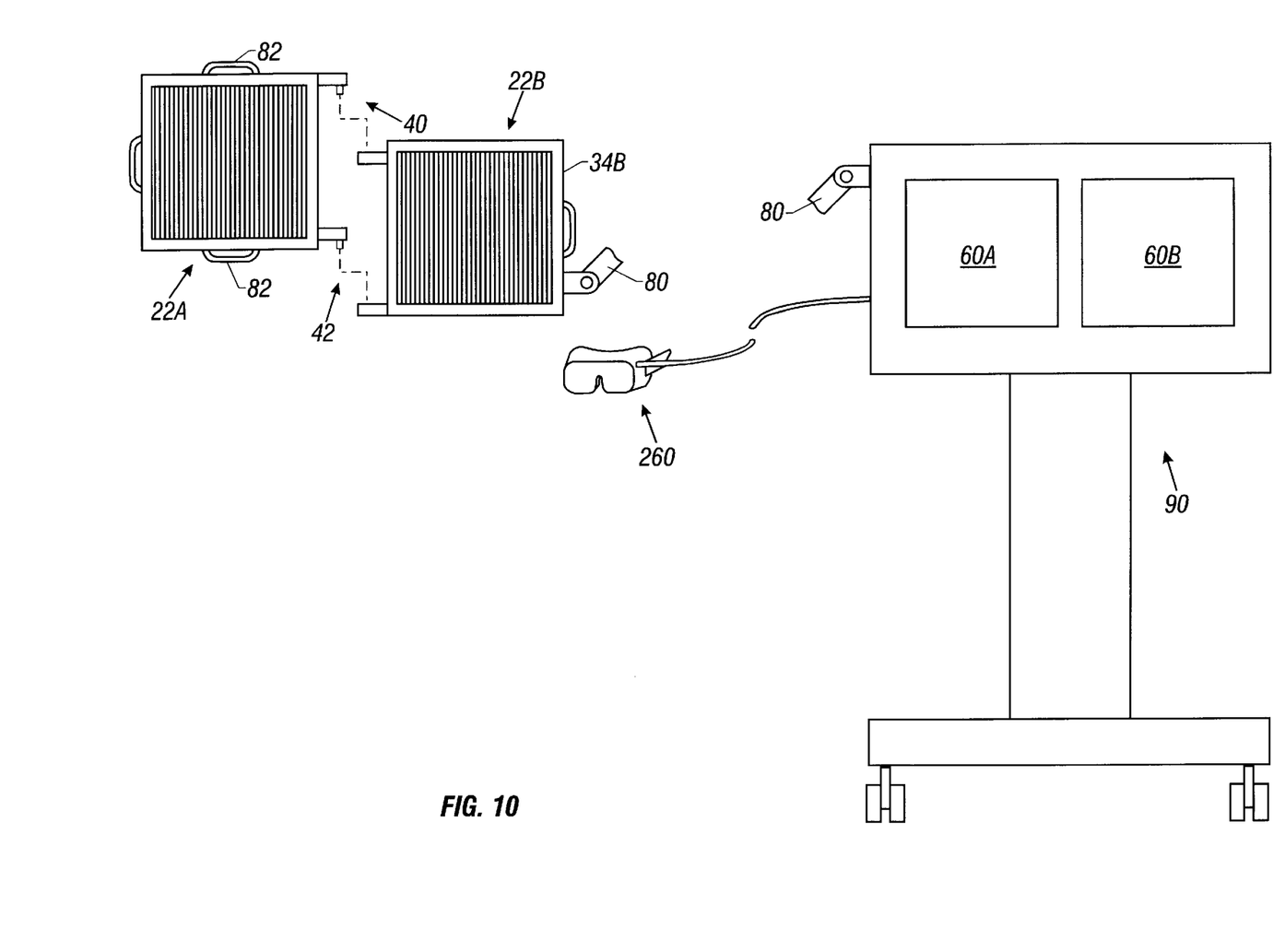
FIG. 10 is a partial, semi-schematic, front view of a gamma camera system with a first head detached from a second head and showing a base unit with monitors.

As shown in FIG. 10, in an exemplary configuration the head 22B is directly supported at its outboard edge by a gantry 80. The second head 22A is only indirectly supported by the gantry via the head 22B and the hinges 40 and 42. The second head 22A may be made readily removable from the head 22B to either allow the head 22B to be used alone, supported by the gantry, or to let the second head 22A be used in a hand-held mode. In this vein, the second head 22A may be provided with one or more handles such as handles 82 at the upper and lower edges of the second head 22A. The handles may also be useful in the positioning of the heads 22A and 22B.

Also shown is a base unit 90 which houses necessary electronics (not shown). This includes signal processing circuitry for receiving signals generated by the detectors when the detectors receive and detect radionuclide emissions, and for processing those signals to generate the displayed images. The base unit also houses or supports one or more monitors 60A and 60B and provides an output for goggles 260. The gantry 80 extends between the base unit 90 and the detector head 22B for supporting the detector heads. Various electrical connectors and conductors, such as cabling (not shown), are provided to couple the heads 22A and 22B to the base unit 90 and its associated electronics. These include connectors formed integrally with the hinges 40 and 42 for providing electrical communication from the head 22A to the head 22B. Alternatively, a jumper cable (not shown) may be connected between the heads 22A and 22B.

Figure 11:
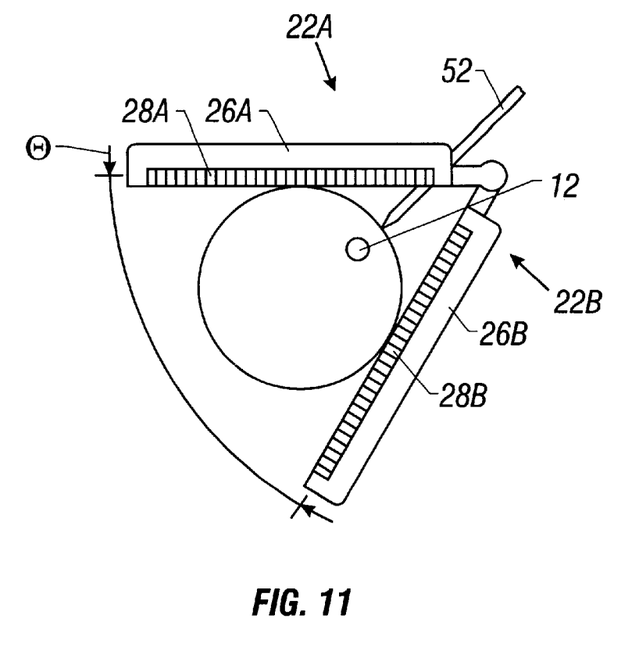
FIGS. 11–14 are partial, semi-schematic, top cross-sectional views of a gamma camera systems shown with first and second heads articulated in a variety of orientations and having a variety of collimator angles.

FIG. 11 shows a configuration of the gamma camera heads 22A and 22B articulated about the hinge axis 200 so that there is an angle θ between the heads. In one such exemplary situation, the heads may be at an acute angle of approximately 45° so as to be positioned around a small body part, e.g., the neck. In this example, the target 12 may be a lymph node in the neck in which suspected cancer cells may be present. The biopsy needle 52 may be introduced not through the gap between the heads but, rather, from below the heads and directed into the examination field. In such a situation, right angle collimators 28A and 28B may be used to provide a high degree of accuracy of biopsy needle placement.

Figure 12:
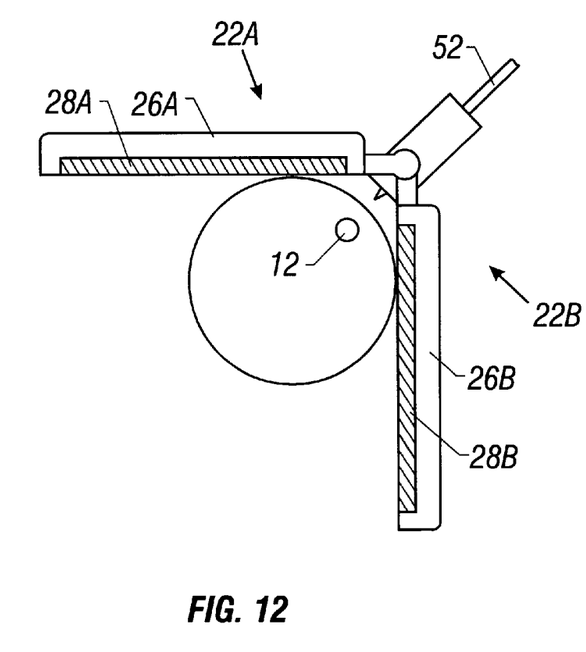

In another exemplary situation shown in FIG. 12, the camera heads are at an angle of approximately 90°. Such an arrangement may also be used for introducing the biopsy needle 52 to a small body part such as the neck. In this example, the needle is inserted through the gap between the camera heads. In this example, collimators having an angle of approximately 45° are provided.

Figure 13:
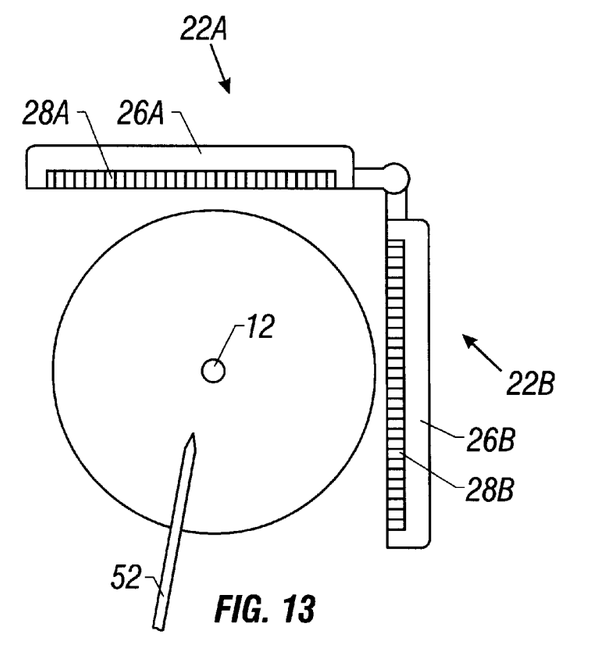

FIG. 13 shows an example of the system configured for use relative to a target 12 in a somewhat larger body part such as a patient's head. In the example, the head faces the detector heads 22A and 22B and the biopsy needle 52 enters from behind the patient's head. In the exemplary configuration, with the detector heads perpendicular to each other, right angle collimators are used.

Figure 14:
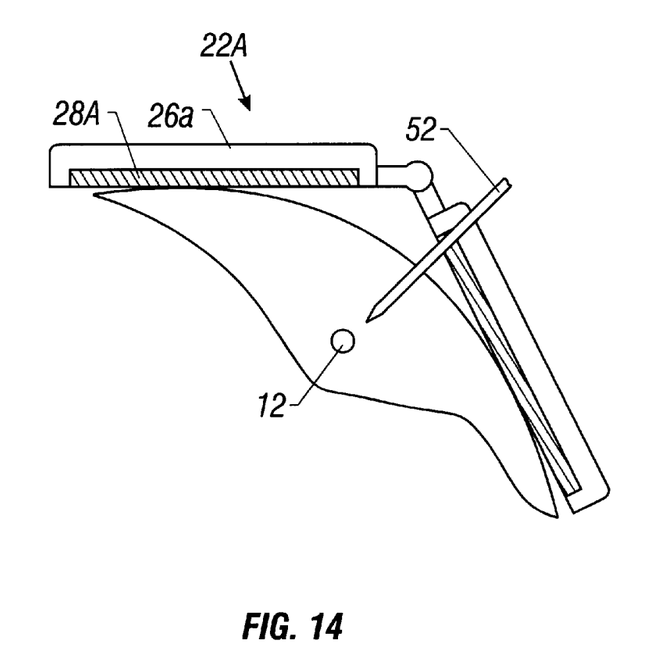

FIG. 14 shows an example of the system configured for use with an even larger body part such as the chest. In the example, the target 12 is a lymph node, such as the axillary lymph node or "sentinel node" under the patient's armpit. The camera heads are placed adjacent the side of the patient's chest and access for the needle 52 may be had through the gap between the heads or from above or below the heads. In the example, the collimators may be preferably be provided with an angle somewhat less than 45°.

Figure 15:
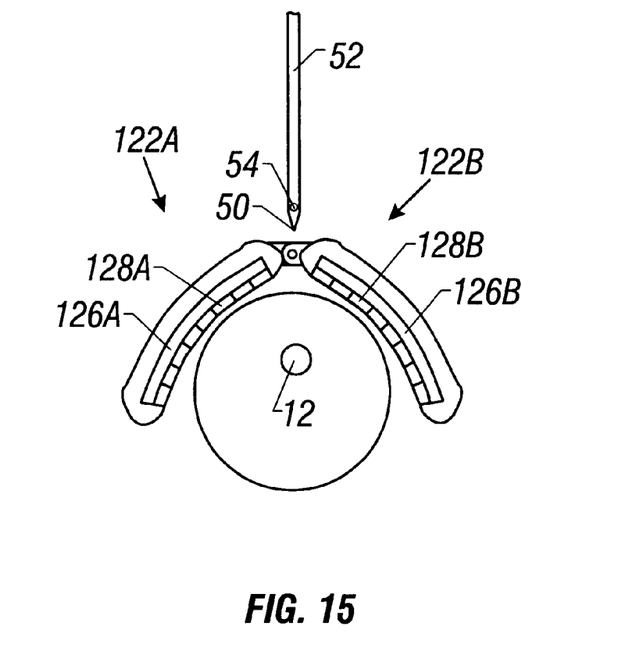
FIG. 15 is a partial, semi-schematic, top cross-sectional view of a gamma camera system.

FIG. 15 shows an alternate system configuration featuring curved heads 122A and 122B. Detector arrays 126A and 126B may be similarly curved, arrayed as if along a section of a surface of a right circular cylinder. Similarly the collimators 128A and 128B are in a position concentric with the detector arrays 126A and 126B so as to provide each head with a field of view that converges.

Figure 16:
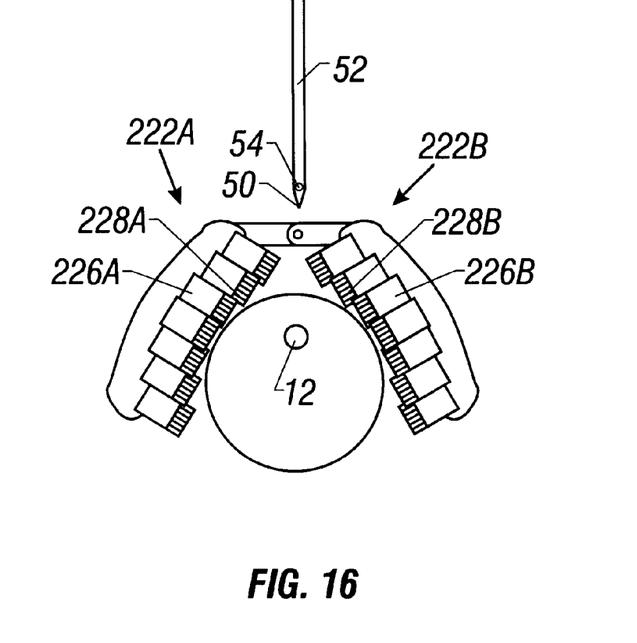
FIG. 16 is a partial, semi-schematic, top cross-sectional view of a gamma camera system.

FIG. 16 shows an alternate embodiment, wherein each head 222A, 222B includes a plurality of detector assemblies 226A, 226B, each having an associated collimator section 228A, 228B. The detector assemblies may be staggered to better conform to the shape of the body part being imaged so as to reduce the distances between the detector assemblies and the body part and thereby provide a clearer image. In the illustrated embodiment, the detectors of each head all face in the same direction as do their collimators so that the images generated remain planar. Optionally, the detector assemblies may be made movable back and forth so that the stagger may be adjusted to conform to individual situations in which the system is used.

For any given patient, the decision as to the appropriate angle between camera heads and the respective collimator angles for each head will depend on factors including: (1) the size and shape of the body part to be imaged; (2) the location (particularly the depth) of the target area in such body part; (3) the position of the patient on an operating table (if any); (4) the path of instrument approach preferred by a surgeon; and (5) the degree of accuracy needed in positioning the instrument. With a large target, e.g., a complex of several large lymph nodes, lower levels of accuracy and image resolution may be sufficient compared to those required for imaging a single small lymph node. Instrument positioning accuracy may largely be maximized when: (1) the two heads are as close as possible to the target (because image resolution decreases with distance); and (2) the greatest useful magnification is provided, such as by selecting collimator angles and head positions so that relatively small movements of the instrument are perceived as relatively large movements across the fields of view of the detectors and thus across the images displayed on the monitors.

A preferred detector is a solid-state device such as a Cadmium Zinc Telluride (CZT) unit. CZT detectors are described in copending U.S. patent application Ser. No. 08/542,883, the disclosure of which is incorporated herein by reference. In an exemplary construction, the faces 30A and 30B may measure approximately 6×6 inches. Particularly convenient sizes may range from 1×1 inches up to greater than 8×8 inches depending on the desired uses. For maximum compactness and ease of use, the housings 24A and 24B will extend only minimally laterally beyond the associated faces 30A and 30B and may include supporting structure for the detectors and collimators as well as any radiation shielding that is provided. In an exemplary embodiment, there may be approximately 0.125 inches or more of lead shielding (not shown) surrounding the detectors on all sides not covered by the collimators. In an exemplary embodiment, the total thickness of the heads would be approximately 2 inches and preferably less than 3 inches (limited only by the thickness of the detectors 76A and 76B, the collimators 28A and 28B, and the housings 24A and 24B with shielding).

A number of embodiments of the present invention have been described. Nevertheless, it will be understood that various modifications may be made without departing from the spirit and scope of the invention. For example, various hinge mechanisms and collimator structures may be utilized. These include dual axis hinge mechanisms, powered articulation of the heads, and more complex collimator structures. Further, there is significant flexibility in the positioning and orientation of the detector heads relative to the patient and the associated selection of collimator angles for the respective detector heads. The selection of head position and orientation and collimator angles will be significantly influenced by anatomical factors. Accordingly, other embodiments are within the scope of the following claims.

What is claimed is:

1. A medical imaging system comprising:
   first and second gamma camera heads, each having a front facing an examination field, the heads articulatable between a first plurality of relative orientations in which a first edge of the first head is aligned and coupled with a first edge of the second head in a parallel spaced-apart relation, defining a gap therebetween of sufficient dimension to permit passage of a biomedical instrument through the gap.

2. The system of claim 1, further comprising:
   a biomedical instrument bearing a radionuclide tag for emitting radiation of a type detectable by the heads, the instrument being constructed to pass through the gap and into the examination field.

3. The system of claim 2, further comprising:
   a sleeve positioned within and passing through the gap and having a first open end facing the examination field and a second open end facing away from the examination field and at least a presterilized internal surface, the biomedical instrument being constructed to pass through the sleeve from without the examination field to within the examination field so that the operative end of the biomedical instrument does not come into contact with the gamma camera heads and thus cannot directly acquire a contaminant from the first and second heads.

4. The system of claim 3, further comprising a display coupled to the first and second gamma camera heads in order to generate a stereoscopic image from emissions received by the first and second heads.

5. The system of claim 4, wherein the display comprises a pair of goggles having left and right display sections.

6. The system of claim 4, wherein the display is constructed to simultaneously display a pair of images on a single screen.

7. The system of claim 6, wherein the display further comprises eyewear to be worn by a user to separate the pair of images.

8. The system of claim 1, further comprising removable collimators mounted within each of the first and second gamma camera heads, respectively.

9. The system of claim 1, further comprising at least one hinge that connects the first and second gamma camera heads to each other.

10. The system of claim 9, wherein the first and second gamma camera heads are hinged to each other for relative movement about an axis fixed relative to the first and second heads.

11. The system of claim 9, wherein the gamma camera heads are hinged to each other by a first hinge located at one end of the first edges of the heads and a second hinge located at a second end of the first edges of the heads, the gap extending substantially continuously between the first and second hinges.

12. The system of claim 9, wherein the second gamma camera head is readily removable from the first gamma camera head.

13. The system of claim 1, further comprising at least one monitor electrically connected to the first and second gamma camera heads, and constructed to display images representative of emissions received by the first and second gamma camera heads.

14. The system of claim 1, wherein the gamma camera heads are flat planar heads.

15. The system of claim 1, wherein the gamma camera heads are curved heads.

16. The system of claim 1, further comprising a gantry directly supporting the first gamma camera head and wherein the second head is indirectly supported by the gantry via the first head.

17. The system of claim 1, wherein at least the first gamma camera head comprises a plurality of detector assemblies, each having an associated collimator, said detector assemblies constructed to be staggered to at least in part conform to a shape of a body part being imaged by the system.

18. The system of claim 1, wherein at least the first gamma camera head has a curved detector array.

19. A method for guiding a biomedical instrument to a target in body comprising:
   providing a radionuclide source at the target;
   providing a radionuclide tag on the instrument;
   providing a gamma camera detector system for receiving and detecting emissions from the source and the tag, wherein providing the gamma camera detector system includes providing first and second gamma camera heads articulatable between a plurality of relative orientations in which a first edge of each head is aligned with the first edge of the other head in a parallel spaced-apart relation, creating a gap therebetween;
   viewing at least one image generated from the emissions; and
   moving the instrument so that a perceived target location and a perceived tag location converge in the image.

20. The method of claim 19, wherein the step of providing the gamma camera detector system further comprising providing first and second collimators having respective first and second collimator angles for the respective first and second heads, the first and second collimators determining respective first and second fields of view of the first and second heads.

21. The method of claim 20, wherein the step of providing the gamma camera detector system comprises: positioning and orienting the first and second heads and selecting said first and second collimator angles so as to substantially fill the first and second fields of view with a region extending at least from the target to a point of entry of the instrument to the body.

22. The method of claim 20, wherein the step of providing the gamma camera detector system comprises: positioning and orienting the first and second heads and selecting the first and second collimator angles so as to substantially fill the field of view with a region extending at least from the target to a region of approach of the instrument to the body.

23. The method of claim 22, wherein the positioning and orienting step is performed in a manner so as to substantially maximize image clarity within said region.

24. The method of claim 20, wherein the moving step comprises moving the instrument so that the perceived tag location and target location converge the at least one image.

25. The method of claim 20, wherein the first and second fields of view at least in part converge, the target being detectable by the first and second gamma camera heads.

26. The method of claim 19 wherein the step of providing a gamma camera detector system comprises providing a first detector array and providing a second detector array having a first field of view and a second detector array having a second field of view, wherein the second field of view is convergent with the first field of view at least in a region including the target.

27. The method of claim 26, wherein the first detector array is provided in a first detector head and the second detector array is provided in a second detector head, wherein the second detector head is movable relative to the first detector head.

28. A medical imaging system comprising:

a first gamma camera head;

a second gamma camera head, in which a first edge of the first head is aligned and coupled with a first edge of the second head;

a first detector array mounted within the first gamma camera head; and a second detector array mounted within the second gamma camera head, the first and second gamma camera heads being articulatable with respect to each other between a first plurality of relative orientations, the first and second gamma camera heads defining a gap therebetween of sufficient dimension to permit passage of a biomedical instrument through the gap.

* * * * *